US009423339B2

(12) United States Patent
Eura et al.

(10) Patent No.: US 9,423,339 B2
(45) Date of Patent: Aug. 23, 2016

(54) SPECTRUM MEASURING DEVICE AND SPECTRUM MEASURING METHOD

(71) Applicant: HAMAMATSU PHOTONICS K.K., Hamamatsu-shi, Shizuoka (JP)

(72) Inventors: Shigeru Eura, Hamamatsu (JP); Kengo Suzuki, Hamamatsu (JP); Kenichiro Ikemura, Hamamatsu (JP); Kazuya Iguchi, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 0 days.

(21) Appl. No.: 14/764,805

(22) PCT Filed: Sep. 17, 2013

(86) PCT No.: PCT/JP2013/075032
§ 371 (c)(1),
(2) Date: Jul. 30, 2015

(87) PCT Pub. No.: WO2014/119037
PCT Pub. Date: Aug. 7, 2014

(65) Prior Publication Data
US 2015/0377770 A1    Dec. 31, 2015

(30) Foreign Application Priority Data
Feb. 4, 2013 (JP) .................. 2013-019406

(51) Int. Cl.
*G01J 1/04* (2006.01)
*G01N 21/31* (2006.01)
(Continued)

(52) U.S. Cl.
CPC ............... *G01N 21/31* (2013.01); *G01J 3/0254* (2013.01); *G01J 3/0291* (2013.01); *G01J 3/42* (2013.01);
(Continued)

(58) Field of Classification Search
CPC ........ G01J 3/42; G01J 3/457; G01N 2201/12; G01N 2201/065; G01N 2201/062; G01N 21/31
USPC .................. 356/236, 432–440, 326; 250/228
See application file for complete search history.

(56) References Cited

U.S. PATENT DOCUMENTS 4,583,860 A    4/1986  Butner
8,525,989 B2 *  9/2013  Iguchi ................... G01N 21/31
                                                     356/326

(Continued)

FOREIGN PATENT DOCUMENTS

JP    H09-292281 A    11/1997
JP    2003-215041 A    7/2003
(Continued)

OTHER PUBLICATIONS

N.C. Greenham et al., "Measurement of absolute photoluminescence quantum efficiencies in conjugated polymers", Chemical Physics Letters, vol. 241, Jul. 14, 1995, p. 89-p. 96.
(Continued)

*Primary Examiner* — Hoa Pham
(74) *Attorney, Agent, or Firm* — Drinker Biddle & Reath LLP (57) ABSTRACT

A spectral measurement apparatus includes a light source for generating a excitation light; an integrator having an input opening portion and an output opening portion; a housing portion arranged in the integrator and for housing a sample; an incidence optical system for making the excitation light incident to the sample; a photodetector for detecting a light to be measured output from the output opening portion; and an analysis means for calculating a light absorptance of the sample, based on a detection value detected by the photodetector, and an irradiation area with the excitation light at a position of incidence to the sample is set larger than an irradiated area of the sample, and the analysis means performs an area ratio correction regarding the irradiation area with the excitation light and the irradiated area of the sample, with respect to the light absorptance calculated.

10 Claims, 9 Drawing Sheets

(51) Int. Cl.
  *G01J 3/44* (2006.01)
  *G01N 21/64* (2006.01)
  *G01J 3/02* (2006.01)
  *G01J 3/42* (2006.01)

(52) U.S. Cl.
  CPC ............ *G01J 3/4406* (2013.01); *G01N 21/645* (2013.01); *G01N 21/6489* (2013.01); *G01N 2021/6469* (2013.01); *G01N 2021/6482* (2013.01); *G01N 2201/062* (2013.01); *G01N 2201/065* (2013.01); *G01N 2201/12* (2013.01)

(56) References Cited

U.S. PATENT DOCUMENTS

| | | | | |
|---|---|---|---|---|
| 8,592,780 | B2* | 11/2013 | Iguchi | G01N 21/645 250/458.1 |
| 2015/0346096 | A1* | 12/2015 | Suzuki | G01N 21/01 250/459.1 |

FOREIGN PATENT DOCUMENTS

| | | |
|---|---|---|
| JP | 2004-309323 A | 11/2004 |
| JP | 2007-086031 A | 4/2007 |
| WO | WO-2012073567 A1 | 6/2012 |

OTHER PUBLICATIONS

Yoshiro Ichino, "Theoretical Analysis of Integrating Sphere-based Absolute Photoluminescence Quantum Efficiency Measurement", The 71st Japan Society of Applied Physics Meeting, 14p-NK-6, Sep. 12, 2010.

John C. de Mello et al., "An improved experimental determination of external photoluminescence quantum efficiency", Advanced Materials, vol. 9, Mar. 3, 1997, p. 230-p. 232.

International Preliminary Report on Patentability dated Aug. 13, 2015 for PCT/JP2013/075032.

* cited by examiner

SPECTRUM MEASURING DEVICE AND SPECTRUM MEASURING METHOD

TECHNICAL FIELD

The present invention relates to a spectral measurement apparatus and a spectral measurement method.

BACKGROUND ART

There is a conventionally-known spectral measurement apparatus configured to irradiate a sample as a measurement object with excitation light and detect light to be measured. As a technology of this kind, for example, Patent Document 1 describes the absolute fluorescence quantum efficiency measurement apparatus configured so that, in obtaining a quantum yield, the sample is fixed at a position where it is not directly hit by the excitation light, in an integrating sphere, and a light absorptance of the sample is obtained from an intensity obtained with indirect incidence of the excitation light to the sample and an intensity obtained with direct incidence of the excitation light to the sample.

Furthermore, for example, Patent Document 2 describes the quantum efficiency measurement apparatus configured to measure the excitation light absorbed by the sample in a state in which the excitation light after passage through the sample is reflected in an integration space and to measure light generated from the sample in a state in which the excitation light after passage through the sample is not reflected in the integration space. This quantum efficiency measurement apparatus performs the two stages of measurement processes, thereby to reduce measurement error due to re-excitation (secondary excitation). Non Patent Documents 1 to 3 describe calculation of quantum yields on the premise that the excitation light is made incident to the sample so as to be included in the sample.

CITATION LIST

Patent Literature

Patent Document 1: Japanese Patent Application Laid-Open No. H9-292281
Patent Document 2: Japanese Patent Application Laid-Open No, 2003-215041

Non Patent Literature

Non Patent Document 1: "Measurement of absolute photoluminescence quantum efficiencies in conjugated polymers Chemical Physics Letters Volume 241", Issues 1-2, 14 Jul. 1995, Pages 89-96, N. C. Greenham, I. D. W. Samuel, G. R. Hayes, R. T. Phillips, Y. A. R. R. Kessener, S. C. Moratti, A. B. Holmes, R. H. Friend
Non Patent Document 2: "An improved experimental determination of external photoluminescence quantum efficiency Advanced Materials", Vol. 9, Issue 3, March 1997, Pages 230-232, John C. de Mello, H. Felix Wittmann, Richard H. Friend
Non Patent Document 3: "Theoretic study on absolute fluorescence quantum efficiency measurement method using integrating sphere", The 71st JSAP Meeting (Sep. 12, 2010), 14p-NK-6, Yoshiro ICHINO (2010, Sep. 12) 14p-NK-6

SUMMARY OF INVENTION

Technical Problem

Here, the foregoing spectral measurement apparatuses are generally constructed under the theory that the excitation light is included in the sample and an irradiation area with the excitation light at a position of incidence to the sample (hereinafter also referred to simply as "irradiation area with the excitation light") is smaller than an irradiated area of the sample, as described above. For this reason, if the irradiation area with the excitation light is made larger than the irradiated area of the sample, e.g., in a case of measuring a small amount of the sample or the like, the calculated light absorptance will be estimated different from a true value and thus it might be difficult to accurately measure the light absorptance.

Therefore, one aspect of the present invention is directed to a problem to provide a spectral measurement apparatus and a spectral measurement method capable of accurately obtaining the light absorptance.

Solution to Problem

In order to solve the above problem, a spectral measurement apparatus according to one aspect of the present invention is a spectral measurement apparatus for irradiating a sample as a measurement object with excitation light and detecting light to be measured, comprising: a light source which generates the excitation light; an integrator having an input opening portion through which the excitation light is input, and an output opening portion from which light reflected inside is output; a housing portion which is arranged in the integrator and which houses the sample; an incidence optical system which makes the excitation light incident to the sample; a photodetector which detects the light output from the output opening portion; and analysis means which calculates a light absorptance of the sample, based on a detection value detected by the photodetector, wherein an irradiation area with the excitation light at a position of incidence to the sample is set larger than an irradiated area of the sample, and wherein the analysis means performs an area ratio correction regarding the irradiation area with the excitation light and the irradiated area of the sample, with respect to the light absorptance calculated.

In this spectral measurement apparatus, the irradiation area with the excitation light can be set larger than the irradiated area of the sample. Furthermore, in this case, the spectral measurement apparatus can implement the area ratio correction regarding the irradiation area with the excitation light and the irradiated area of the sample, with respect to the light absorptance calculated. Therefore, the light absorptance can be accurately obtained, for example, even in the case of measuring a small amount of the sample.

The excitation light may be applied to the sample so as to include the sample. In this regard, the area ratio correction can be performed by multiplying the light absorptance by a value obtained by dividing the irradiation area with the excitation light by the irradiated area of the sample. Furthermore, the analysis means can calculate the light absorptance, based on a relational expression of the area ratio correction according to the following formula (1):

[Math 1]

$$A = \rho \times \frac{S_2}{S_1} \times \left( \frac{Abs_{22} - Abs_{12}}{1 - Abs_{12}} \right) + (1 - \rho) \quad (1)$$

where
A: the light absorptance, $\rho$=reflectance of the integrator, $S_1$: the irradiated area of the sample, $S_2$: the irradiation area with the excitation light, Abs$_{12}$: the light absorptance in indirect excitation, and Abs$_{22}$: the light absorptance in direct excitation.

A specific example of a configuration for suitably achieving the foregoing operational effect is a configuration wherein the incidence optical system adjusts the excitation light so that the irradiation area with the excitation light is larger than the irradiated area of the sample.

A spectral measurement method according to one aspect of the present invention is a spectral measurement method for irradiating a sample as a measurement object with excitation light and detecting light to be measured, comprising: a step of arranging the sample in an integrator; a step of applying the excitation light into the integrator to make the excitation light incident to the sample so that an irradiation area with the excitation light at a position of incidence to the sample is larger than an irradiated area of the sample; a step of detecting light output from the integrator, with a photodetector; and a step of calculating a light absorptance of the sample, based on a detection value detected by the photodetector, wherein the step of calculating the light absorptance comprises a step of performing an area ratio correction regarding the irradiation area with the excitation light and the irradiated area of the sample, with respect to the light absorptance.

This spectral measurement method also achieves the foregoing operational effect that it becomes feasible to accurately obtain the light absorptance.

The step of making the excitation light incident to the sample may comprise applying the excitation light so as to include the sample. In this regard, the area ratio correction can be performed by multiplication the light absorptance by a value obtained by dividing the irradiation area with the excitation light by the irradiated area of the sample. Furthermore, the step of calculating the light absorptance can comprise calculating the light absorptance, based on a relational expression of the area ratio correction according to the following formula (2):

[Math 2]

$$A = \rho \times \frac{S_2}{S_1} \times \left( \frac{Abs_{22} - Abs_{12}}{1 - Abs_{12}} \right) + (1 - \rho) \quad (2)$$

where

A: the light absorptance, ρ=reflectance of the integrator, S$_1$: the irradiated area of the sample, S$_2$: the irradiation area with the excitation light, Abs$_{12}$: the light absorptance in indirect excitation, and Abs$_{22}$: the light absorptance in direct excitation.

Advantageous Effects of Invention

The one aspect of the present invention has made it feasible to accurately obtain the light absorptance.

BRIEF DESCRIPTION OF DRAWINGS

FIG. 8 includes (a) a graph showing an example of a wavelength spectrum detected in the absence of a sample, (b) a graph showing an example of a wavelength spectrum detected in indirect excitation, and (c) a graph showing an example of a wavelength spectrum detected in direct excitation.

FIG. 9 includes (a) a schematic view showing an example of relationship between an irradiation area with excitation light and an irradiated area of the sample, and (b) a schematic view showing another example of the relationship between the irradiation area with the excitation light and the irradiated area of the sample.

DESCRIPTION OF EMBODIMENTS

A preferred embodiment will be described below in detail with reference to the drawings. In the below description, identical or equivalent elements will be denoted by the same reference symbols, without redundant description.

Figure 1:
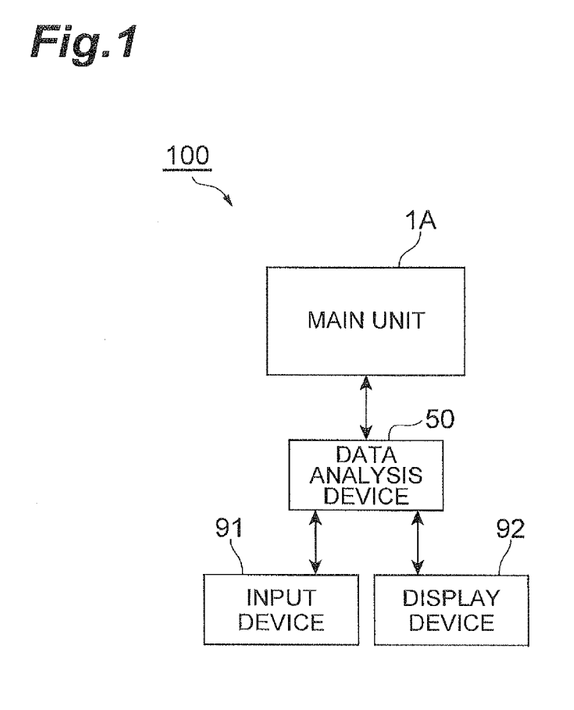
FIG. 1 is a drawing schematically showing a configuration of a spectral measurement apparatus according to an embodiment.

FIG. 1 is a drawing schematically showing a configuration of a spectral measurement apparatus according to an embodiment. As shown in FIG. 1, the spectral measurement apparatus 100 according to the present embodiment is an apparatus that measures or evaluates luminescence characteristics such as fluorescence characteristics by the photoluminescence method (PL method), for a sample as a sample to be a measurement object. The sample can be, for example, one of organic EL (Electroluminescence) materials and fluorescent materials such as luminescence materials for white LED (Light Emitting Diode), for FPD (Flat Panel Display), and so on and it can be, for example, of a powder form, a liquid form (solution form), a solid form, or a thin film form. The spectral measurement apparatus 100 has a main unit 1A, a data analysis device 50, an input device 91, and a display device 92.

Figure 2:
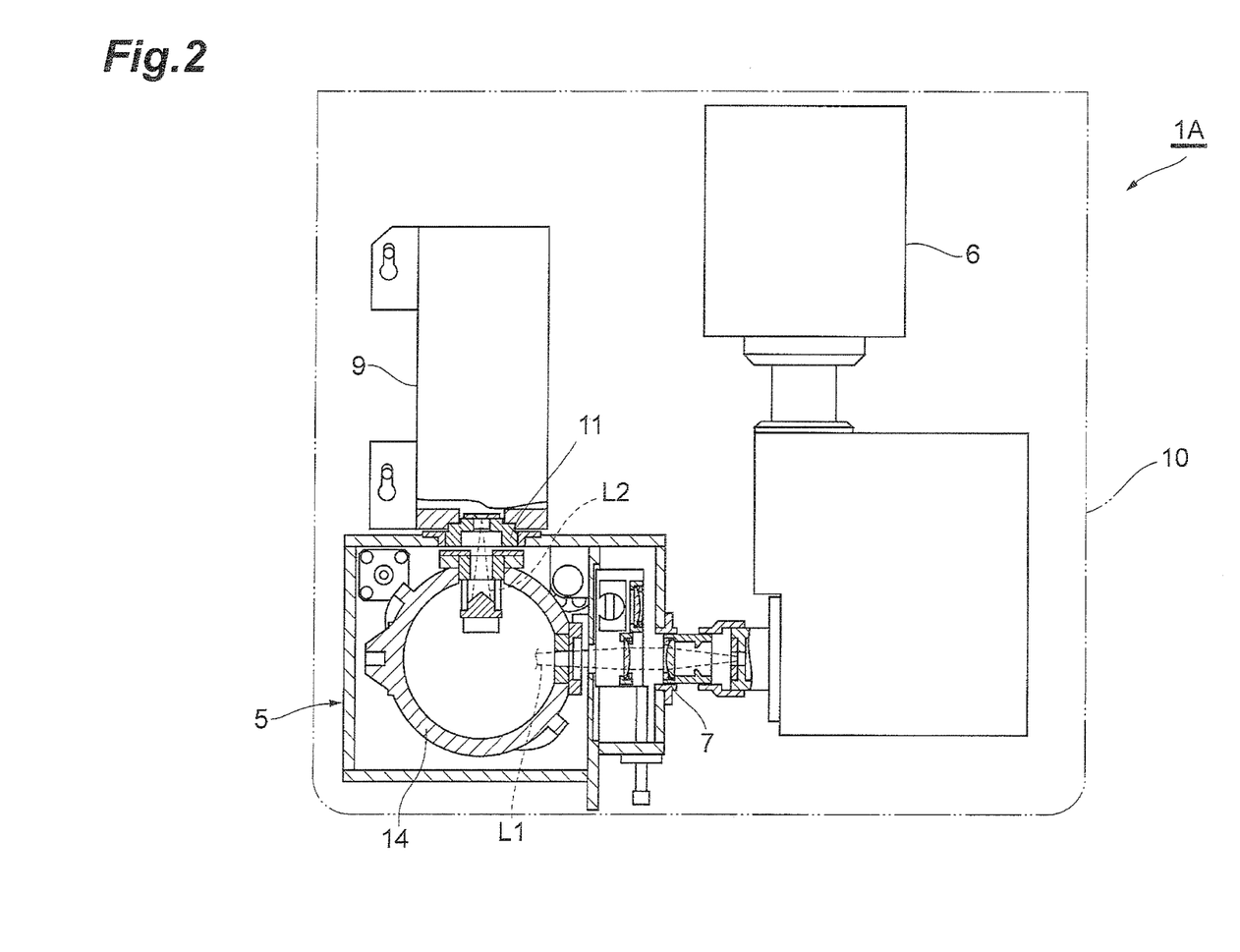
FIG. 2 is a plan view showing a main unit in indirect excitation.
Figure 3:
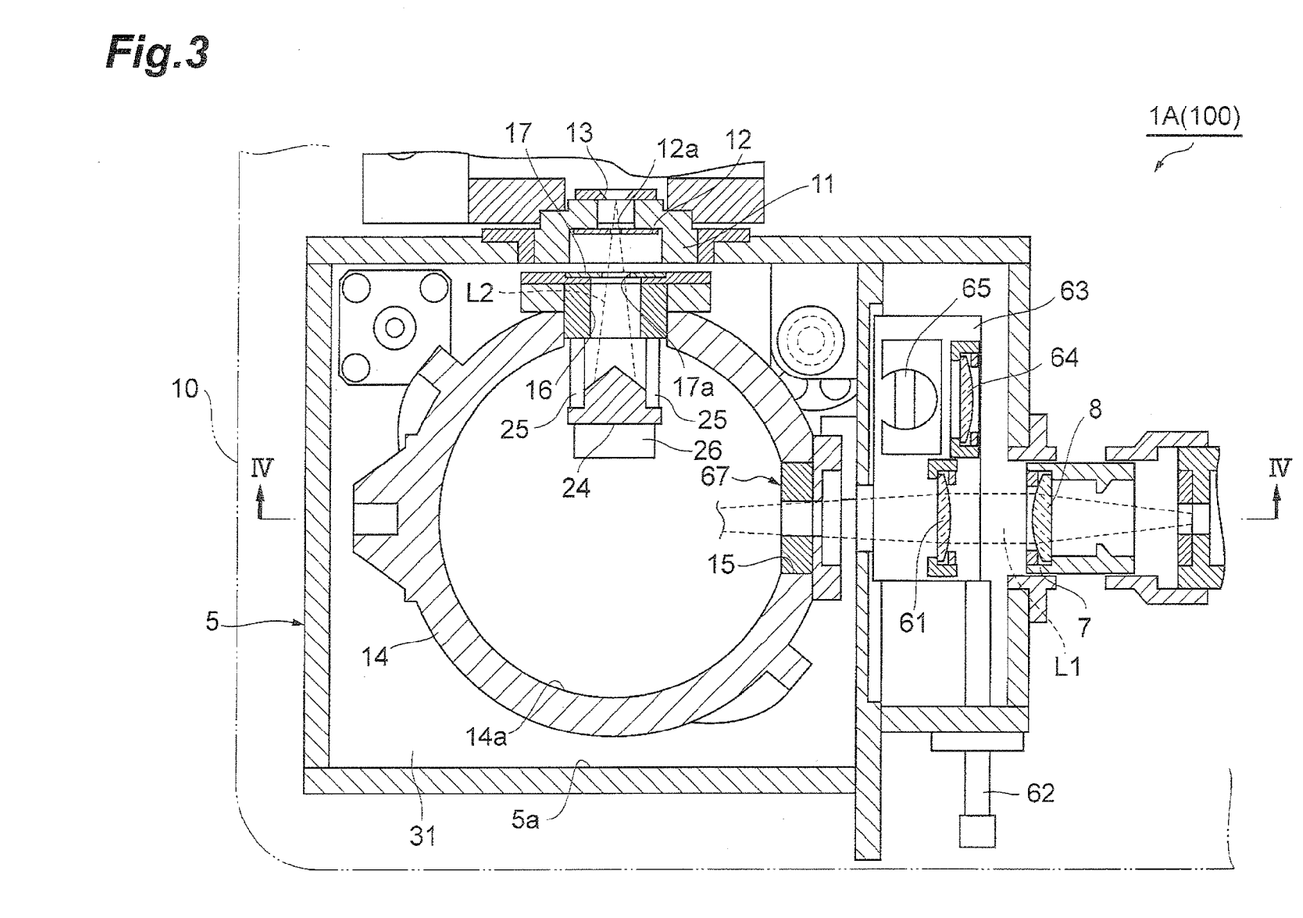
FIG. 3 is an enlarged view of internal and surrounding portions of a dark box in FIG. 2.
Figure 4:
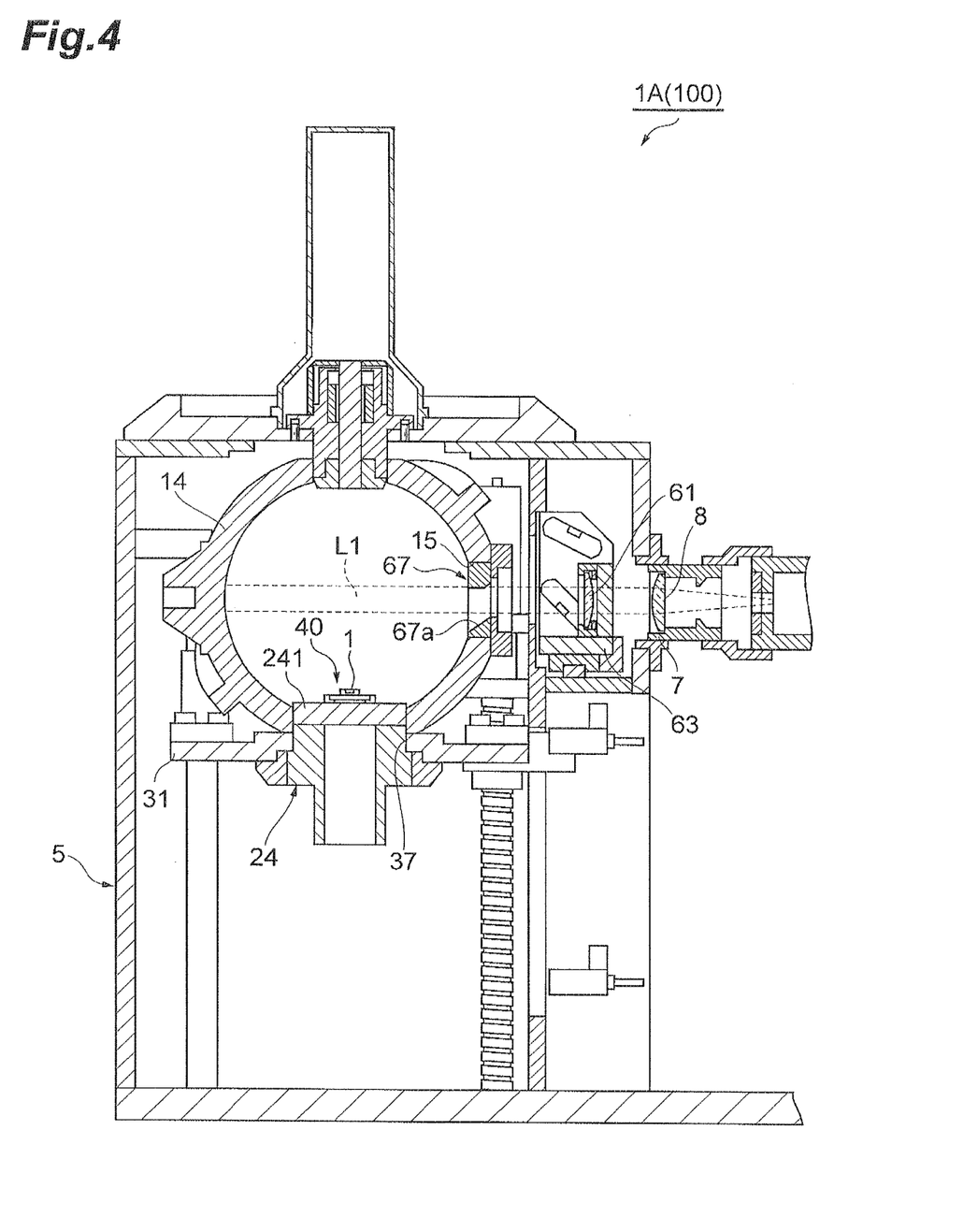
FIG. 4 is a cross-sectional view along the line IV-IV in FIG. 3.

FIG. 2 is a plan view showing the main unit in indirect excitation, FIG. 3 an enlarged view of internal and surrounding portions of a dark box in FIG. 2, and FIG. 4 a cross-sectional view along the line IV-IV in FIG. 3. As shown in FIGS. 2 to 4, the main unit 1A is configured to irradiate the sample 1 with excitation light L1 of a predetermined wavelength and detect light to be measured L2 generated in response to the irradiation. This main unit 1A has a dark box 5.

The dark box 5 is a box of a rectangular parallelepiped shape made of metal and blocks entrance of light from the outside. An inner surface 5a of the dark box 5 is provided with a coating or the like of a material that absorbs the excitation light L1 and the light to be measured L2. A light output portion 7 of a light generation unit 6 is connected to one side wall of the dark box 5. The light generation unit 6 is an excitation light source, for example, configured by a xenon lamp, a spectroscope, and so on, and generates the excitation light L1. The excitation light L1 is collimated by a lens 8 provided at the light output portion 7, to be input into the dark box 5.

A light input portion 11 of a light detection unit (photodetector) 9 is connected to a rear wall of the dark box 5. The light detection unit 9 is a multi-channel detector, for example, configured by a spectroscope, a CCD sensor, and so on and detects the light to be measured L2. The light to be measured L2 is narrowed down by an opening part 12a of an aperture being a stop member 12 provided at the light input portion 11, and is input through a slit 13 into the light detection unit 9.

An integrating sphere (integrator) 14 is arranged in the dark box 5. The integrating sphere 14 is provided with a coating of a high diffuse reflection agent such as barium sulfate on its inner surface 14a or is made of a material such as PTFE or Spectralon. The integrating sphere 14 is formed with a light input opening (input opening portion) 15 through which the excitation light L1 is input and with a light output opening (output opening portion) 16 from which the light to be measured L2 is output. The excitation light L1 is condensed by a lens 61 in the dark box 5 in indirect excitation and guided through the light input opening 15 into the integrating sphere 14. The light to be measured L2 is narrowed down by an opening 17a being an aperture of a stop member 17 provided at the light output opening 16 and is output to the outside of the integrating sphere 14.

The dark box 5, light generation unit 6, and light detection unit 9 described above are enclosed in a housing 10 made of metal. The optical axis of the excitation light L1 output from the light output portion 7 of the light generation unit 6 and the optical axis of the light to be measured L2 input into the light input portion 11 of the light detection unit 9 are approximately perpendicular to each other in a horizontal plane.

An opening 37 is formed in the lower part of the integrating sphere 14 and in a stage 31 to which the integrating sphere 14 is fixed. The opening 37 is equipped with a sample container holder (sample holder) 24 which is detachably attached thereto from the bottom of the stage 31. Namely, the sample container holder 24 is detachably attached to the integrating sphere 14. The sample container holder 24 has a sample table 241 which supports a sample container 40 as mounted thereon.

Figure 5:
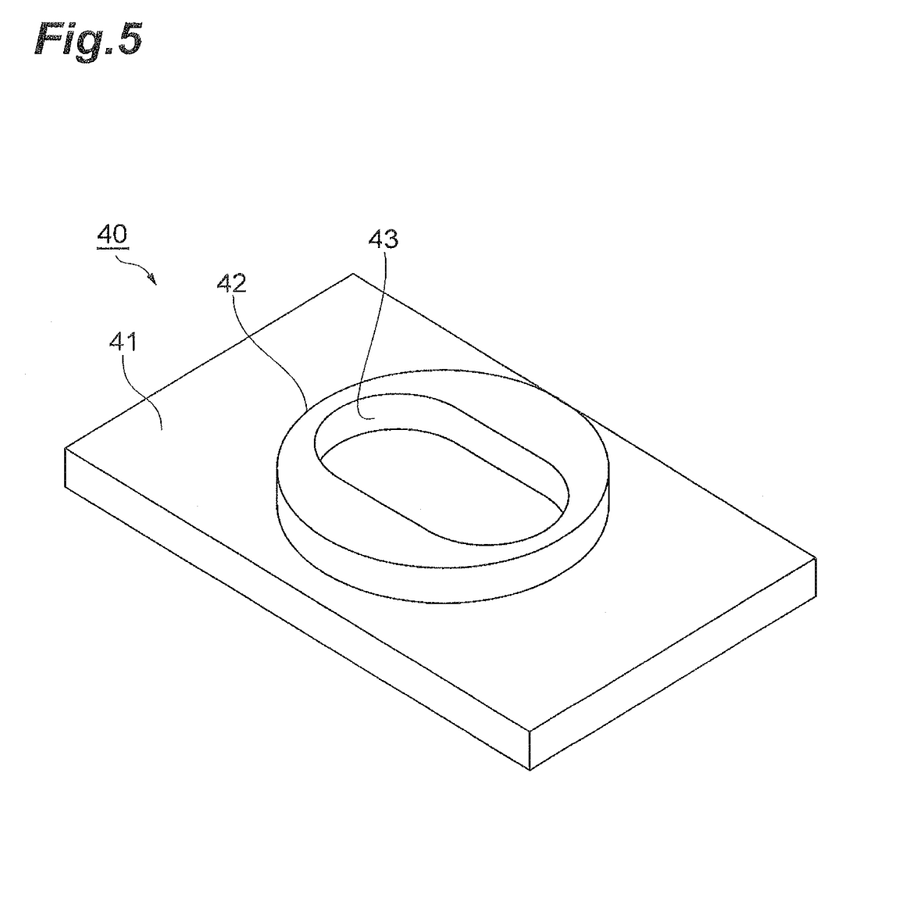
FIG. 5 is a perspective view showing an example of a sample container.

FIG. 5 is a perspective view showing an example of the sample container. As shown in FIG. 5, the sample container 40 is a container that is used in measurement making use of the integrating sphere 14, and has a flange portion 41 of a rectangular plate shape (e.g., a rectangle), a projected portion 42 provided on the flange portion 41, and a housing portion 43 provided in the projected portion 42 and serving as a depressed portion for housing the sample 1. The shape of the flange portion 41 does not have to be limited to the rectangular shape but may be another shape such as a circular shape or an elliptical shape. The sample container 40 of this configuration can be manufactured by fixing a cylindrical member with a through hole in its central part onto a plate member by adhesion or the like. By this, a portion of the plate member where the cylindrical member is not bonded becomes the flange portion 41, and the through hole of the cylindrical member becomes the housing portion 43 as a depressed portion for housing the sample 1. This manufacturing method allows us to relatively easily manufacture the sample container 40.

This sample container 40 is made, for example, of a transparent material such as quartz or synthetic quartz because it is favorable for purposes including suppression of absorption of light by the sample container 40. It is noted that the sample container 40 does not have to be perfectly transparent. The projected portion 42 has a circular outer shape when viewed from top and its cross section is circular. The housing portion 43, when viewed from top, has an oblong shape elongated in the longitudinal direction of the flange portion 41 (which is, in other words, a track shape having the same long axis as the flange portion 41). Namely, a long axis direction of a plane defined by an opening of the housing portion 43 (hereinafter referred to as opening plane of the housing portion 43) is identical to a long axis direction of the flange portion 41. The shape of the opening plane of the housing portion 43 does not have to be limited to the oblong shape, but may be any shape having along axis, such as a rectangular shape or an elliptical shape. Since the opening plane of the housing portion 43 has the shape having the long axis, the opening area can be made larger. This housing portion 43 can house the sample 1 so that the excitation light L1 to be applied to the sample 1 includes the sample 1.

Figure 6:
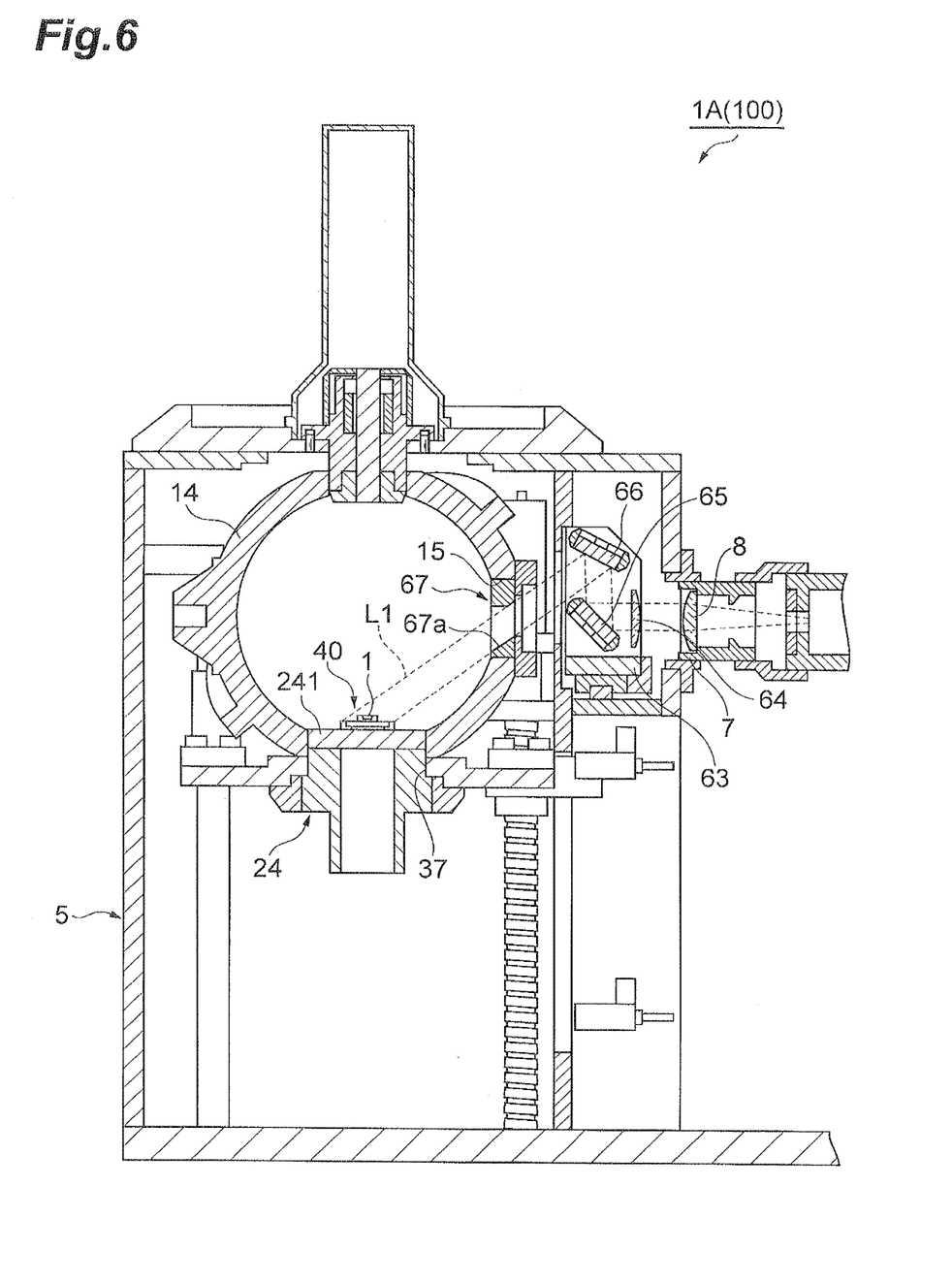
FIG. 6 is a cross-sectional view corresponding to FIG. 4 in direct excitation.

FIG. 6 is a cross-sectional view corresponding to FIG. 4 in direct excitation. As shown in FIG. 6, the main unit 1A in the present embodiment has a handle 62 (cf. FIG. 3) as optical path changeover means for change in optical path of the excitation light L1. In the main unit 1A, a stage 63 is moved by this handle 62 to switch the lens 61 to a collimator lens 64. The excitation light L1 condensed by the collimator lens 64 is successively reflected by mirrors 65, 66 to be guided into the integrating sphere 14.

An aperture 67 is provided at the light input opening 15 of the integrating sphere 14. A cut portion 67a is formed in at least a part of an opening portion of the aperture 67. The shape of the cut portion 67a is made so that the excitation light L1 passing through the aperture 67 to impinge upon the sample 1 becomes wider than a region of the sample 1 (the area of the sample 1 on a top plan view). In other words, the aperture 67 is formed in such a shape as not to interrupt the excitation light L1, and the opening portion thereof is inclined so as to expand toward the downstream side of the irradiation optical axis.

These collimator lens 64, mirrors 65, 66, and aperture 67 constitute an incidence optical system for making the excitation light L1 incident to the sample 1. In this incidence optical system, the excitation light L1 input into the dark box 5 is collimated by the collimator lens 64, successively reflected by the mirrors 65, 66, and guided through the aperture 67 into the integrating sphere 14, whereby the excitation light L1 is applied to the sample container 40 so as to include the sample 1, in the integrating sphere 14.

Figure 9:
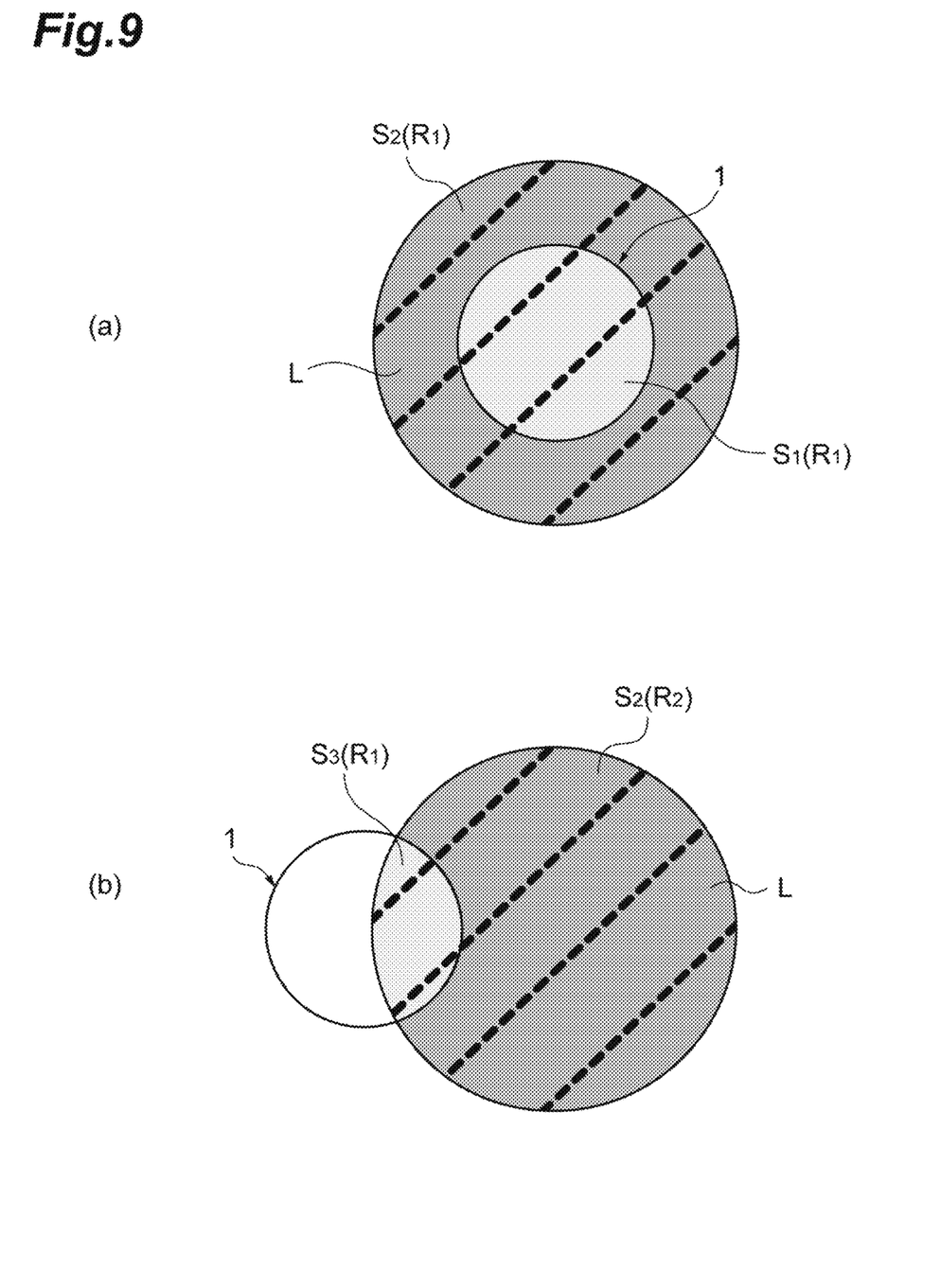

As shown in FIG. 9, the irradiation area $S_2$ with the excitation light L1 is an area of an irradiation region $R_2$ with the excitation light L1 at the position of incidence to the sample 1, and the irradiated area of the sample 1, $S_1$ or $S_3$, is an area of an irradiated region $R_1$ where the sample L1 is irradiated with the excitation light L1.

Referring back to FIG. 1, the data analysis device 50 is an analysis means that performs a data analysis necessary for a wavelength spectrum (detection values) acquired by the light detection unit 9, to acquire information about the sample 1. The data analysis device 50 herein calculates the light absorptance of the sample 1, based on an output from a spectral analysis device 30, and performs an area ratio correction regarding the irradiation area with the excitation light L1 and the irradiated area of the sample 1, with respect to the light absorptance calculated (details of which will be described later).

The input device 91 is used for input of instructions for the data analysis and others, or for input of analysis conditions and others, and is connected to the data analysis device 50. The display device 92 is used for display of the data analysis result obtained and others, and is connected to the data analysis device 50.

Figure 7:
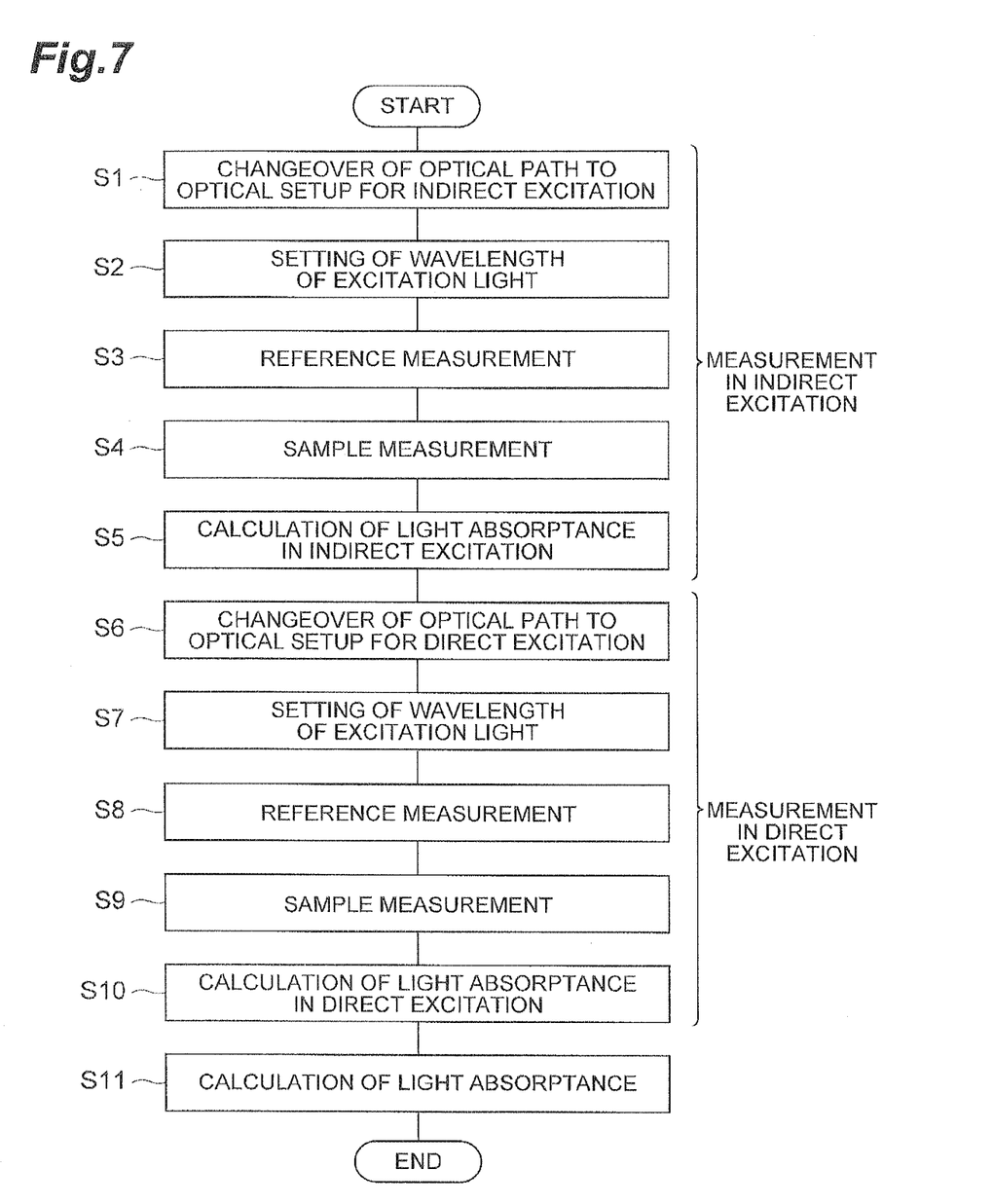
FIG. 7 is a flowchart showing a spectral measurement method using the spectral measurement apparatus in FIG. 1.

Next, the spectral measurement method by the above-described spectral measurement apparatus 100 will be described below with reference to the flowchart of FIG. 7.

[Measurement in Indirect Excitation]

First performed is measurement in indirect excitation, i.e., in a state in which the sample 1 is not directly irradiated with the excitation light L1. For example, by manipulation of a path changeover switch or the like, the handle 62 is actuated to move the stage 63 so as to realize an optical setup where the lens 61 is arranged on the optical axis of the excitation light L1 (S1, cf. FIG. 4). In conjunction therewith, the wavelength of the excitation light L1 is set to a predetermined wavelength (S2).

Figure 8:
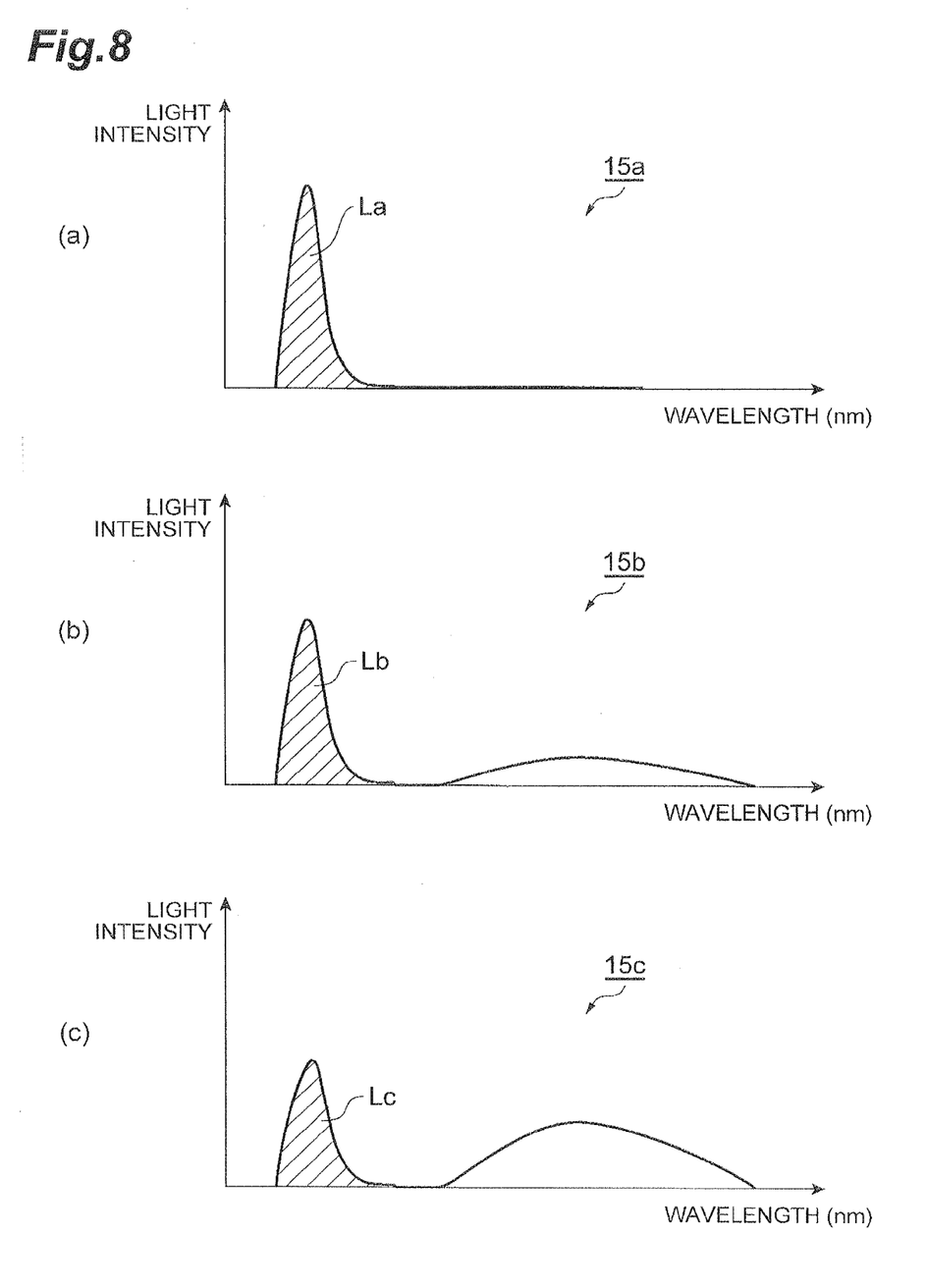

Then, reference measurement is performed which is spectral measurement in a state in which the sample container 40 is not mounted (i.e., in the absence of the sample 1) (S3). Specifically, the light is emitted from the light generation unit 6 and the excitation light L1 is input into the integrating sphere 14. This excitation light L1 is not directly incident to the sample 1 but arrives directly at the inner surface of the integrating sphere 14. Then, the light, after multiple diffuse reflections inside the integrating sphere 14, is output from the light output opening 16 to the light detection unit 9 to obtain a wavelength spectrum 15a (cf. (a) in FIG. 8) by the light detection unit 9. Since this wavelength spectrum 15a has the intensity in an excitation wavelength region, the intensity in the excitation wavelength region is integrated by the data analysis device 50 to acquire an excitation light region intensity La in the absence of the sample 1.

Next, the sample 1 is housed in the sample container 40 and this sample container 40 is placed on a sample table 241 of the sample container holder 24. Then, sample measurement is carried out which is spectral measurement in direct excitation in a state in which the sample 1 is arranged in the integrating sphere 14 (S4). Specifically, the light is emitted from the light generation unit 6 and the excitation light L1 is input into the integrating sphere 14. This excitation light L1 is not directly incident to the sample 1 but arrives directly at the inner surface of the integrating sphere 14 (cf. FIG. 4). Then, the light, after multiple diffuse reflections inside the integrating sphere 14, is output from the light output opening 16 to the light detection unit 9 to obtain a wavelength spectrum 15b (cf. (b) in FIG. 8) by the light detection unit 9. Subsequently, the data analysis device 50 integrates the intensity in the excitation wavelength region to acquire an excitation light region intensity Lb in indirect excitation.

Next, based on the acquired intensities La and Lb, the light absorptance in indirect excitation is calculated by the data analysis device 50 (S5). Specifically, the light absorptance $Abs_1$ in indirect excitation is calculated in accordance with the following formula.

$$Abs_1 = 1 - Lb/La$$

[Measurement in Direct Excitation]

Next, measurement is carried out in direct excitation or in a state in which the sample 1 is directly irradiated with the excitation light L1. For example, by manipulation of the path changeover switch or the like, the handle 62 is actuated to move the stage 63 to realize an optical setup where the collimator lens 64 is arranged on the optical axis of the excitation light L1 (S6, cf. FIG. 6). In conjunction therewith, the wavelength of the excitation light L1 is set to the predetermined wavelength (S7).

Then, reference measurement is performed in the same manner as in above S3 to acquire an excitation light region intensity La in the absence of the sample 1 (S8). Then, sample measurement is carried out to acquire an excitation light region intensity Lc in direct excitation (S9). Specifically, the light is emitted from the light generation unit 6 and the excitation light L1 is input into the integrating sphere 14, whereby the excitation light L1 is applied to the sample 1 on the sample container holder 24.

At this time, the excitation light L1 travels through the collimator lens 64 and passes through the aperture 213, so as to be applied to the sample 1 in a state in which its spot diameter is wider than the region of the sample 1; that is, the irradiation area $S_2$ with the excitation light L1 is larger than the irradiated area $S_1$ of the sample 1, and the excitation light L1 is applied to the sample 1 so as to include the sample 1 (cf. FIGS. 6 and 9).

Subsequently, the light, after multiple diffuse reflections inside the integrating sphere 14, is output from the light output opening 16 to the light detection unit 9 to obtain a wavelength spectrum 15c (cf. (c) in FIG. 8) by the light detection unit 9. The light to be measured L2 herein contains luminescence such as fluorescence generated in the sample 1 in response to the irradiation with the excitation light L1, and components of light resulting from scattering, reflection, etc. by the sample 1 out of the excitation light L1. Then, the data analysis device 50 integrates the intensity in the excitation wavelength region to acquire an excitation light region intensity Lc in direct excitation.

Next, based on the acquired intensities La and Lc, the light absorptance in direct excitation is calculated by the data analysis device 50 (S10). Specifically, the light absorptance $Abs_2$ in direct excitation is calculated in accordance with the following formula.

$$Abs_2 = 1 - Lc/La$$

Finally, the light absorptance A of the sample 1 is calculated (S11). In the present embodiment herein the apparatus is configured to perform an area ratio correction regarding the irradiation area $S_2$ with the excitation light Ll and the irradiated area $S_1$ of the sample 1 (hereinafter referred to simply as "area ratio correction") on the occasion of calculating the light absorptance. This area ratio correction is carried out based on multiplication of the light absorptance by "irradiated area $S_2$/irradiation area $S_1$". Here, the light absorptance A is calculated based on a relational expression of the area ratio correction according to the following formula (3).

[Math 3]

$$A = \rho \times \frac{S_2}{S_1} \times \left( \frac{Abs_{22} - Abs_{12}}{1 - Abs_{12}} \right) + (1 - \rho) \quad (3)$$

In this formula,

A: light absorptance, $\rho$: reflectance of the integrator (reflectance at the excitation wavelength of the inner wall material of the integrating sphere 14), $Abs_{12}$: light absorptance in indirect excitation, and $Abs_{22}$: light absorptance in direct excitation.

Here, it is common sense in the field of the spectral measurement apparatus 100 that the irradiation area $S_2$ with the excitation light L1 is smaller than the irradiated area $S_1$ of the sample 1, and in general spectrometry, the theory is established on the premise of this common sense. Therefore, when the irradiation area $S_2$ with the excitation light L1 is larger than the irradiated area $S_1$ of the sample 1, there is a possibility that the light absorptance by general spectrometry becomes smaller than an accurate value (true value). Therefore, after a great deal of diligent study on this theory, we found such knowledge that it is necessary to make a correction for the light absorptance A by the area ratio of the irradiated area $S_1$ of the sample 1 and the irradiation area $S_2$ with the excitation light L1.

Namely, the present embodiment is one accomplished based on the foregoing knowledge, and when the irradiation area $S_2$ with the excitation light L1 is larger than the irradiated area $S_1$ of the sample 1, the area ratio correction is made for the light absorptance A calculated, whereby the light absorptance A can be obtained with accuracy.

In the present embodiment, as described above, the light absorptance A is accurately obtained when the irradiation area $S_2$ with the excitation light L1 is larger than the irradiated area $S_1$ of the sample 1; for this reason, it becomes feasible to accurately measure the light absorptance A even in the case of the sample 1 being provided in a small amount. Therefore, the present embodiment is believed to be also effective, particularly, to measurement of the sample 1 in a small amount. Namely, the present embodiment applies the area correction method to the measurement of absorptance using the integrating sphere 14, thereby enabling the measurement of a sample in a small amount.

In passing, it can also be contemplated in the case of measuring a small amount of sample 1 that the depth of the housing portion 43 of the sample container 40 is decreased while maintaining the irradiated area $S_1$, but in this case, the sample 1 becomes more likely to be scattered; therefore, it is not practical, at least, in terms of usability.

In the present embodiment, the excitation light L1 is applied to the sample 1 so as to include the sample 1, but the present invention is not limited to this example. For example, by adjusting at least one of the incidence optical system of the excitation light L1 and the shape of the housing portion 43 of the sample container 40, the excitation light L1 may be applied so as to overlap with a part of the sample 1 (cf. (b) in FIG. 9), under the condition that the irradiation area $S_2$ with the excitation light L1 is larger than the irradiated area $S_1$ of the sample 1.

At this time, the foregoing operation by the data analysis device 50, with implementation of the area ratio correction in calculation of the light absorptance, may be configured to calculate the light absorptance A, based on a relational expression of the area ratio correction according to the following formula (4). Specific description of the following formula (4) will be given below.

[Math 4]

$$A = \rho \times \frac{S_2}{S_3} \times \left( \frac{Abs_{23} - Abs_{13}}{1 - Abs_{13}} \right) + (1 - \rho) \quad (4)$$

In the formula,
$Abs_{13}$: light absorptance in indirect excitation, and
$Abs_{23}$: light absorptance in direct excitation.

Next, the above formulas (3), (4) will be specifically explained.

When the excitation light L1 is applied so as to include the whole of the sample 1, as shown in (a) in FIG. 9, a relational expression between area-weighted average reflectance $T_2$ and light absorptance $A_2$ of the sample 1 is defined by the following formula (5).

[Math 5]

$$T_2 = 1 - A_2 \quad (5)$$

Therefore, the calculation equation of "de Mello's light absorptance" obtained in the foregoing Non Patent Document 2 is given by the following formula (6). It can be said that the calculation equation of "de Mello's light absorptance" cancels the physical process of the integrating sphere 14. In the following formula (6), the "de Mello's light absorptance" is equal to 1−relative reflectance ($T_2/\rho$).

[Math 6]

$$A = 1 - \frac{L_{c2}}{L_{b2}} = 1 - \frac{(1 - A_2)}{\rho} = 1 - \frac{T_2}{\rho} \quad (6)$$

In this formula,
$Lb_2$: excitation light region intensity in indirect excitation, and
$Lc_2$: excitation light region intensity in direct excitation.

When consideration is given using the physical model wherein the physical process of the integrating sphere 14 is cancelled, an actually measured reflectance $Tr_2$ is obtained as the relative reflectance as represented by the following formula (7). An actually measured light absorptance $Ar_2$ is obtained as (1−relative reflectance) as represented by below formula (8).

[Math 7]

$$T_{r2} = \frac{T_2}{\rho} \quad (7)$$

[Math 8]

$$A_{r2} = 1 - T_{r2} = 1 - \frac{T_2}{\rho} \quad (8)$$

The area-weighted average reflectance $T_2$ is defined by the following formula (9) and formula (10) below is derived from the following formula (9).

[Math 9]

$$T_2 = \frac{S_1}{S_2} \times T_t + \frac{S_2 - S_1}{S_2} \rho \quad (9)$$

[Math 10]

$$1 - \frac{T_2}{\rho} = \frac{S_1}{S_2} \times \left( 1 - \frac{T_t}{\rho} \right) \quad (10)$$

By substituting the above formula (10) into the above formula (8), formula (11) below is derived. By substituting the relational expression "$T_t = 1 - A$" between the absolute reflectance $T_t$ and light absorptance A of the sample 1 into the below formula (11), below formulas (12) and (13) are derived and, below formula (14) is derived from the above formula (6) and above formula (8). The below formula (14) means that the true light absorptance $A_t$ of the sample 1 can be calculated if the "de Mello's light absorptance" is obtained by experiment, the value thereof is corrected by the area ratio correction $S_2/S_1$, and the integrator reflectance $\rho$ being the absolute reflectance at the excitation wavelength of the integrating sphere 14 is known.

[Math 11]

$$1 - \frac{T_t}{\rho} = \frac{S_2}{S_1} \times A_{r2} \quad (11)$$

-continued

[Math 12]

$$1 - \frac{1-A_t}{\rho} = \frac{S_2}{S_1} \times A_{r2} \qquad (12)$$

[Math 13]

$$A_t = \rho \times \frac{S_2}{S_1} \times A_{r2} + (1-\rho) \qquad (13)$$

[Math 14]

$$A_t = \rho \times \frac{S_2}{S_1} \times \left(1 - \frac{L_{c2}}{L_{b2}}\right) + (1-\rho) \qquad (14)$$

On the other hand, when the excitation light L1 is applied so as to overlap with a part of the sample 1 and the irradiation area $S_2$ is larger than the irradiated area $S_3$ as shown in (b) in FIG. 9, a relational expression between the area-weighted average reflectance $T_3$ and light absorptance $A_3$ of the sample 1 is defined by the following formula (15).

[Math 15]

$$T_3 = 1 - A_3 \qquad (15)$$

Therefore, the calculation equation of "de Mello's light absorptance" is given by the following formula (16). It can be said that the calculation equation of "de Mello's light absorptance" cancels the physical process of the integrating sphere 14. In the following formula (16), the "de Mello's light absorptance" is equal to 1−relative reflectance ($T_3/\rho$).

[Math 16]

$$A = 1 - \frac{L_{c3}}{L_{b3}} = 1 - \frac{(1-A_3)}{\rho} = 1 - \frac{T_3}{\rho} \qquad (16)$$

In this formula, $Lb_3$: excitation light region intensity in indirect excitation, and $Lc_3$: excitation light region intensity in direct excitation.

When consideration is given using the physical model wherein the physical process of the integrating sphere 14 is cancelled, an actually measured reflectance $Tr_3$ is obtained as the relative reflectance as represented by the following formula (17). An actually measured light absorptance $Ar_3$ is obtained as (1−relative reflectance) as represented by below formula (18).

[Math 17]

$$T_{r3} = \frac{T_3}{\rho} \qquad (17)$$

[Math 18]

$$A_{r3} = 1 - T_{r3} = 1 - \frac{T_3}{\rho} \qquad (18)$$

The area-weighted average reflectance $T_3$ is defined by the following formula (19) and formula (20) below is derived from the following formula (19).

[Math 19]

$$T_3 = \frac{S_3}{S_2} \times T_t + \frac{S_2 - S_3}{S_2} \rho \qquad (19)$$

[Math 20]

$$1 - \frac{T_3}{\rho} = \frac{S_3}{S_2} \times \left(1 - \frac{T_t}{\rho}\right) \qquad (20)$$

By substituting the above formula (20) into the above formula (18), below formula (21) is derived. By substituting the relational expression "$T_t = 1 - A$" between the absolute reflectance $T_t$ and light absorptance A of the sample 1 into the below formula (21), below formulas (22) and (23) are derived and, below formula (24) is derived from the above formula (16) and above formula (18). The below formula (24) means that the true light absorptance $A_t$ of the sample 1 can be calculated if the "de Mello's light absorptance" is obtained by experiment, the value thereof is corrected by the area ratio correction $S_2/S_3$, and the integrator reflectance $\rho$ at the excitation wavelength of the integrating sphere 14 is known.

[Math 21]

$$1 - \frac{T_t}{\rho} = \frac{S_2}{S_3} \times A_{r3} \qquad (21)$$

[Math 22]

$$1 - \frac{1-A_t}{\rho} = \frac{S_2}{S_3} \times A_{r3} \qquad (22)$$

[Math 23]

$$A_t = \rho \times \frac{S_2}{S_3} \times A_{r3} + (1-\rho) \qquad (23)$$

[Math 24]

$$A_t = \rho \times \frac{S_2}{S_3} \times \left(1 - \frac{L_{c3}}{L_{b3}}\right) + (1-\rho) \qquad (24)$$

Formula (25) below is obtained from the calculation equation "$A = (1-A_t)/\rho = 1 - T_t/\rho$" of the "de Mello's light absorptance" and the relational expression "$A_r = 1 - T_r = 1 - T_t/\rho$" of the actually measured light absorptance (1−relative reflectance). Furthermore, formula (26) below is obtained from the above formulas (6) and (8). In addition, formula (27) below is obtained from the above formulas (16) and (18). The "de Mello's light absorptance" is equivalent to determination of the light absorptance (1−relative reflectance) actually measured with primary reflection.

[Math 25]

$$A_r = 1 - \frac{T_r}{\rho} = 1 - \frac{L_c}{L_b} = \text{de Mello's absorptance } A \qquad (25)$$

[Math 26]

$$A_{r2} = 1 - \frac{T_2}{\rho} = 1 - \frac{L_{c2}}{L_{b2}} = \text{de Mello's absorptance } A \qquad (26)$$

[Math 27]

$$A_{r3} = 1 - \frac{T_3}{\rho} = 1 - \frac{L_{c3}}{L_{b3}} = \text{de Mello's absorptance } A \quad (27)$$

Formula (28) below is obtained from the relational expression "$A_r = 1-T_r = 1-T_t/\rho$" of the actually measured light absorptance (1-relative reflectance) and the above formula (11). By substituting the above formulas (25) and (26) into it, we obtain formula (29) below.

[Math 28]

$$A_r = \frac{S_2}{S_1} \times A_{r2} \quad (28)$$

[Math 29]

$$1 - \frac{L_c}{L_b} = \frac{S_2}{S_1} \times \left(1 - \frac{L_{c2}}{L_{b2}}\right) \quad (29)$$

Formula (30) below is obtained from the relational expression "$A_r = 1-T_r = 1-T_t/\rho$" of the actually measured light absorptance (1-relative reflectance) and the above formula (21). By substituting the above formulas (25) and (27) into it, we obtain formula (31) below.

[Math 30]

$$A_r = \frac{S_2}{S_3} \times A_{r3} \quad (30)$$

[Math 31]

$$1 - \frac{L_c}{L_b} = \frac{S_2}{S_3} \times \left(1 - \frac{L_{c3}}{L_{b3}}\right) \quad (31)$$

The above formulas (29) and (31) indicate that a measurement in each optical condition corrected by the area correction coefficient becomes equivalent to the "de Mello's light absorptance" in the measurement condition that the irradiated area $S_1$ of the sample 1 is not less than the irradiation area $S_2$ with the excitation light L1.

Therefore, in the optical condition that the irradiation area $S_2$ with the excitation light L1 is larger than the irradiated area $S_1$ of the sample 1 and the excitation light L1 includes the sample 1 (cf. (a) in FIG. 9), the true value $A_t$ of light absorptance (true light absorptance) can be determined by below formula (32). Furthermore, in the optical condition that the irradiation area $S_2$ with the excitation light L1 is larger than the irradiated area $S_1$ of the sample 1 and the excitation light L1 overlaps with a part of the sample 1 (cf. (b) in FIG. 9), the true value $A_t$ of light absorptance (true light absorptance) can be determined by below formula (33).

[Math 32]

$$A_t = \rho \times \frac{S_2}{S_1} \times \left(1 - \frac{L_{c2}}{L_{b2}}\right) + (1-\rho) \quad (32)$$

[Math 33]

$$A_t = \rho \times \frac{S_2}{S_3} \times \left(1 - \frac{L_{c3}}{L_{b3}}\right) + (1-\rho) \quad (33)$$

When an approximation of $\rho=1$ is valid, the above formula (32) is simplified into below formula (34) and the above formula (33) into below formula (35), allowing the true value $A_t$ of light absorptance to be determined thereby.

[Math 34]

$$A_t = \frac{S_2}{S_1} \times \left(1 - \frac{L_{c2}}{L_{b2}}\right) \quad (34)$$

[Math 35]

$$A_t = \frac{S_2}{S_3} \times \left(1 - \frac{L_{c3}}{L_{b3}}\right) \quad (35)$$

Here, it is sometimes difficult to directly obtain the foregoing intensities $L_{b2}$, $L_{c2}$, $L_{b3}$, and $L_{c3}$ by experiment; for example, there is a case where the intensity varies upon changeover between the optical path in indirect excitation and the optical path in direct excitation. In this case, the reflectance or light absorptance that can be experimentally measured can be used as a measurement parameter.

Namely, as to the true value $A_t$ of light absorptance, the reflectance R can be used as a measurement parameter in each optical condition, whereby the above formula (32) is translated into below formula (36) and the above formula (33) into below formula (37). Concerning the true value $A_t$ of light absorptance, when the light absorptance Abs is used as a measurement parameter in each optical condition, the above formula (32) is transformed into the above formula (3) and the above formula (33) into the above formula (4).

[Math 36]

$$A_t = \rho \times \frac{S_2}{S_1} \times \left(1 - \frac{R_{22}}{R_{12}}\right) + (1-\rho) \quad (36)$$

[Math 37]

$$A_t = \rho \times \frac{S_2}{S_3} \times \left(1 - \frac{R_{23}}{R_{13}}\right) + (1-\rho) \quad (37)$$

In the above formulas, $R_{12}$: reflectance in indirect excitation=$L_{b2}/L_a$, $R_{22}$: reflectance in direct excitation=$L_{c2}/L_a$, $R_{13}$: reflectance in indirect excitation=$L_{b3}/L_a$, and $R_{23}$: reflectance in direct excitation=$L_{c3}/L_a$.

The above described the preferred embodiment but it should be noted that the present invention is by no means intended to be limited to the above embodiment but may be modified without change in the spirit and scope of the invention as described in each of the claims, or may be applied to others.

For example, the above embodiment was configured so that, for changeover between the measurement in indirect excitation and the measurement in direct excitation, the optical system was driven to change the optical arrangement thereof; but, instead thereof or in addition thereto, the sample 1 (sample container 40) may be moved. Furthermore, the above embodiment used the integrating sphere 14 as integrator, but the integrator may be any means (optical component) for spatially integrating light inside it; for example, the integrating hemisphere disclosed in Japanese Patent Application Laid-open Publication No. 2009-103654 may be adopted. In the above embodiment the sample container holder 24 attached to the integrator held the sample container 40 having the housing portion 43, but the sample holder having the housing portion 43 may be attached to the integrator.

The above embodiment may be modified so as to obtain the light absorptance A by implementation of either of area ratio corrections expressed by the following formulas.

$$A = S_2/S_1 \times A'$$

$$A = \rho \times S_2/S_1 \times A' + (1-\rho)$$

In these equations,

A': light absorptance before the correction.

The above embodiment may be provided with a lens for expanding the excitation light L1 from the light output portion 7, in order to make the irradiation area $S_2$ larger than the irradiated area $S_1$. The above embodiment is equipped with the collimator lens 64, mirrors 65, 66, and aperture 67 as the incidence optical system but it may be modified so as to be equipped with the aperture 67 only. Furthermore, since the expanded excitation light L1 is output from the light output portion 7, the incidence optical system may be configured including the output end of the light output portion 7 (or may be composed of it only).

The above embodiment may be configured to perform the measurement in direct excitation (the foregoing S6 to the foregoing S10) before the measurement in indirect excitation (the foregoing S1 to the foregoing S5), and these measurements may be performed in random order. The above embodiment needs only to be configured so that the irradiation area $S_2$ with the excitation light L1 is larger than the irradiated area $S_1$ of the sample 1, and the irradiation area $S_2$ can be made larger than the irradiated area $S_1$, for example, by adjusting at least one of the incidence optical system of the excitation light L1 and the shape of the housing portion 43 of the sample container 40.

INDUSTRIAL APPLICABILITY

The one aspect of the present invention has made it feasible to accurately obtain the light absorptance.

REFERENCE SIGNS LIST

1—sample, 6—light generation unit (light source), 9—light detection unit (photodetector), 14—integrating sphere (integrator), 15—light input opening (input opening portion), 16—light output opening (output opening portion), 43—housing portion, 50—data analysis device (analysis means), 64—collimator lens (incidence optical system), 65, 66—mirrors (incidence optical system), 67—aperture (incidence optical system), 100—spectral measurement apparatus, L1—excitation light, L2—light to be measured, $S_1$—irradiated area of sample, $S_2$ irradiation area with excitation light.

The invention claimed is:

1. A spectral measurement apparatus for irradiating a sample as a measurement object with excitation light and detecting light to be measured, comprising:
a light source configured to generate the excitation light;
an integrator having an input opening portion for inputting the excitation light, and an output opening portion for outputting the light to be measured;
a sample container including a housing portion for housing the sample and arranged in the integrator;
an incidence optical system configure to irradiate the sample with the excitation light so that an irradiation area with the excitation light at a position of incidence to the sample is set larger than an irradiated area of the sample;
a photodetector configured to detect the light to be measured output from the output opening portion and output a detection signal; and
an analyzer configured to calculate a light absorptance of the sample, based on the detection signal, wherein the analyzer performs an area ratio correction regarding the irradiation area with the excitation light and the irradiated area of the sample, with respect to the light absorptance calculated.

2. The spectral measurement apparatus according to claim 1, wherein the incidence optical system irradiates the sample with the excitation light so as to include the sample.

3. The spectral measurement apparatus according to claim 2, wherein the analyzer multiplies the light absorptance by a value obtained by dividing the irradiation area with the excitation light by the irradiated area of the sample for the area ration correction.

4. The spectral measurement apparatus according to claim 3, wherein the analyzer calculates the light absorptance, based on a relational expression of the area ratio correction according to the following formula (1):

[Math 1]

$$A = \rho \times \frac{S_2}{S_1} \times \left(\frac{Abs_{22} - Abs_{12}}{1 - Abs_{12}}\right) + (1 - \rho) \qquad (1)$$

where

A: the light absorptance, $\rho$=reflectance of the integrator, $S_1$: the irradiated area of the sample, $S_2$: the irradiation area with the excitation light, $Abs_{12}$: the light absorptance in indirect excitation, and $Abs_{22}$: the light absorptance in direct excitation.

5. The spectral measurement apparatus according to claim 1, wherein the integrator comprises an integrating sphere or an integrating hemisphere.

6. A spectral measurement method for irradiating a sample as a measurement object with excitation light and detecting light to be measured, comprising:
arranging the sample in an integrator;
irradiating the sample with the excitation light so that an irradiation area with the excitation light at a position of incidence to the sample is larger than an irradiated area of the sample;
detecting the light to be measured output from the integrator, with a photodetector and outputting a detection signal; and
calculating a light absorptance of the sample, based on the detection signal, wherein the calculating performs an area ratio correction regarding the irradiation area with the excitation light and the irradiated area of the sample, with respect to the light absorptance.

7. The spectral measurement method according to claim 6, wherein the irradiating irradiates the sample with the excitation light so as to include the sample.

8. The spectral measurement method according to claim 7, wherein the calculating comprises multiplying the light absorptance by a value obtained by dividing the irradiation area with the excitation light by the irradiated area of the sample for the area ratio correction.

9. The spectral measurement method according to claim 7, wherein the calculating comprises calculating the light absorptance, based on a relational expression of the area ratio correction according to the following formula (2):

[Math 2]

$$A = \rho \times \frac{S_2}{S_1} \times \left( \frac{Abs_{22} - Abs_{12}}{1 - Abs_{12}} \right) + (1 - \rho) \quad (2)$$

where

A: the light absorptance, $\rho$=reflectance of the integrator, $S_1$: the irradiated area of the sample, $S_2$: the irradiation area with the excitation light, $Abs_{12}$: the light absorptance in indirect excitation, and $Abs_{22}$: the light absorptance in direct excitation.

10. The spectral measurement method according to claim 6, wherein the integrator comprises an integrating sphere or an integrating hemisphere.

* * * * *